US00PP20303P2

(12) United States Plant Patent
Carruth

(10) Patent No.: US PP20,303 P2
(45) Date of Patent: Sep. 15, 2009

(54) MINIATURE ROSE PLANT NAMED 'WEKGLEZNEO'

(50) Latin Name: *Rosa hybrida*
Varietal Denomination: WEKglezneo

(75) Inventor: Thomas F. Carruth, Altadena, CA (US)

(73) Assignee: Weeks Wholesale Rose Grower, Inc., Pomona, CA (US)

( * ) Notice: Subject to any disclaimer, the term of this patent is extended or adjusted under 35 U.S.C. 154(b) by 0 days.

(21) Appl. No.: 12/214,368

(22) Filed: Jun. 17, 2008

(51) Int. Cl.
*A01H 5/00* (2006.01)

(52) U.S. Cl. ..... Plt./121

(58) Field of Classification Search ..... Plt./121
See application file for complete search history.

*Primary Examiner*—Susan B McCormick Ewoldt

(57) ABSTRACT

A new variety of Miniature rose suitable for garden decoration, having flowers of orange pink with a glowing yellow reverse coloration.

1 Drawing Sheet

Classification: The present invention relates to a new *Rosa hybrida* plant.

Variety denomination: The new plant has the varietal denomination 'WEKglezneo'.

BACKGROUND OF THE INVENTION

This invention relates to a new and distinct variety of Miniature Rose. It has an undisseminated seedling of my creation as its seed parent with the following genetic origin Golden Holstein×Livin' Easy and as its pollen parent the variety known as 'WEKemilcho' (U.S. Plant Pat. No. 15,256).

SUMMARY OF THE INVENTION

Among the features which distinguish the new variety from other presently available and commercial rose cultivars known to the inventor are the following combinations of characteristics: its unique orange pink with a glowing yellow reverse flowers coloration, its red suffusion on the inner surface of the sepal that appears as the flower ages, its cuspidate petal apices, its green style and its hairy rachis. The plant has a bushy compact moderately upright growing habit, suitable for outdoor garden decoration.

Asexual reproduction of the new variety by budding as performed in Kern County and Pomona, Calif., shows that the foregoing and other distinguishing characteristics come true to form and are established and transmitted through succeeding asexual propagations. 'WEKglezneo' may be asexually propagated by cuttings, budding and grafting. The budding and grafting successfully occurred on the plant/rootstock *Rosa hybrida* cv. 'Dr. Huey' (not patented).

COMPARISON WITH PARENTS

The new rose may be distinguished from its seed parent, an undisseminated seedling of my creation by the following combination of characteristics: whereas 'WEKglezneo' bears medium size flowers (about 4.0 to about 6.8 cm. in diameter) of orange pink with a glowing yellow reverse coloration, the undisseminated seedling bears significantly larger flowers (about 7.1 to about 9.2 cm. in diameter) of pure yellow coloration. The new variety is classified as a miniature rose with a bushy compact moderately upright low growing habit (about 46 to about 56 cm. in height), whereas the seed parent is classified as a floribunda rose with a significantly taller rounded bushy growing habit (about 88 to about 105 cm. in height).

The new variety may be distinguished from its pollen parent, 'WEKemilcho' by the following combination of characteristics: whereas 'WEKglezneo' bears medium size flowers (about 4.0 to about 6.8 cm. in diameter) of orange pink with a glowing yellow reverse coloration, 'WEKemilcho' bears significantly smaller flowers (about 3.6 to about 4.7 cm. in diameter) of scarlet red coloration with a yellow "eyezone". The new variety bears double flowers (about 17 to 24 petals), whereas the pollen parent bears flowers with significantly lesser petalage (about 5 to 6 petals).

COMPARISON WITH THE CLOSEST COMMERCIALLY AVAILABLE CULTIVAR

The new variety may be distinguished from its closest commercially available cultivar, 'BAIprez' (U.S. Plant Pat. No. 16,408) by the following combination of characteristics: whereas 'WEKglezneo' bears medium size flowers (about 4.0 to about 6.8 cm. in diameter) of orange pink with a glowing yellow reverse coloration, 'BAIprez' bears significantly larger flowers (about 7.0 to 9.0 cm. in diameter) of reflexed yellow-orange petals that are strongly bordered in red. The new variety is classified as a miniature rose with a bushy compact moderately upright low growing habit (about 46 to about 56 cm. in height), whereas the closest commercially available cultivar is classified as a floribunda rose with a significantly taller compact and bushy growing habit.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society (1966)

except where common terms of color definition are employed.

DESCRIPTION OF THE NEW VARIETY

The following description is of 3 to 4 year-old rose plants of the new variety grown outdoors in Pomona, Calif. in the month of May. Phenotypic expression may vary with environmental, cultural and climatic conditions, as well as differences in conditions of light and soil.

FLOWER

The new variety sometimes bears its flowers singly, usually in clusters of two to five or more per stem. Flowers may be borne in regular rounded clusters on strong short stems (about 11 to about 26 cm.). Outdoors, the plant blooms abundantly and nearly continuously during the growing season. The flowers have a slight tea fragrance.

BUD

The peduncle is about 2.0 to about 2.8 cm. in length, of somewhat slender to average caliper (about 0.1 to about 0.2 cm. in diameter), and usually erect. It is moderately rough, with some stipitate glands and some hairs. Peduncle color is between 146B and 146A often moderately suffused, especially on the side exposed to the sun, with between 187B and 183B.

Before the calyx breaks, the bud is about 0.7 to about 1.2 cm. in diameter at the widest point, about 1.1 to about 1.6 cm. in length, and pointed in shape. The surface of the bud bears few foliaceous appendages and some hairs, usually with slender entire foliaceous parts extending beyond the tip of the bud about ½ or more of its length. Bud color is between 137C and 146A sometimes lightly suffused, especially on the side exposed to the sun, with between 187A and 183A.

The sepals are about 1.5 to about 2.2 cm. in length and about 0.5 to about 0.8 cm. in width at the widest point. The outer surface color of the sepal is between 137C and 146A sometimes lightly suffused, especially on the side exposed to the sun, with between 187A and 183A. The inner surface color of the sepal is near 138B broadly bordered by near 139A. After the sepals open, the inner surface color is often moderately suffused, especially on the area exposed to the sun, with between 187A and 187B. The inner surface of the sepal is covered with fine wooly tomentum; sepal margins are lined with few stipitate glands and numerous hairs.

The receptacle of the flower is of medium length (about 0.4 to about 0.5 cm.) and moderately thin in caliper (about 0.4 to about 0.5 cm. in diameter). The receptacle is urn-shaped to moderately globular in form. Its surface is very smooth with some hairs and thick fleshy walls. The receptacle color is between 144A and 146A sometimes moderately suffused, especially on the side exposed to the sun, with between 187A and 183A.

As the petals open (after the calyx breaks), the bud is about 0.9 to about 1.6 cm. in diameter at the widest point, about 1.5 to about 2.0 cm. in length, and moderately ovoid to somewhat globular in form. The color at the base of the under surfaces of the newly opened petals is between 12A and 12B gradually suffusing toward the center of the petals with between 20B and 20C often blushed mostly on the outermost petals with between 53C and 53D. The color of the upper surfaces of the newly opened petals is between 53B and 53C. At the point where the petal attaches, there is a large zone of between 9B and 13B.

BLOOM

When fully open, the bloom ranges from about 4.0 to about 6.8 cm. in diameter. Petalage is double with about 17 to 24 petals and about 2 to 4 petaloids irregularly arranged. When partially open, the bloom form is moderately globular to cupped, and the petals are loosely spiraled to somewhat cupped with petal edges somewhat reflexed outward. When fully open, the bloom form is cupped, and the petals are loosely cupped with petal edges somewhat reflexed outward.

PETALS

The substance of the petals is moderately heavy and of somewhat thick thickness, with upper surfaces moderately satiny to somewhat shiny and under surfaces slightly shiny. The petals are about 1.2 to about 2.5 cm. in length and about 0.9 to about 2.1 cm. in width at the widest point. Petal margins are entire.

The outer petals are obovate in shape with cuspidate apices. The inner petals are moderately obovate to somewhat oblanceolate in shape with usually cuspidate and sometimes rounded apices.

Petaloids are about 0.8 to about 1.2 cm. in length and about 0.4 to about 0.6 cm. in width at the widest point. Petaloids are irregularly shaped moderately obovate to somewhat subulate with rounded apices.

NEWLY OPENED FLOWER

On the under surfaces of the outer, intermediate and inner petals, the color at the base of the petals is between 10A and 9C, gradually suffusing toward the center of the petals with between 19B and 20C often blushed mostly on the outermost petals with between 53B and 53C. There is no visible change in coloration at the point where the petal attaches on the under surface. The upper surface color of the outer, intermediate and inner petals is between 53D and 46C. At the point where the petal attaches, there is a large zone of between 8A and 13B.

The under and upper surface color of the petaloids are similar in coloration to the upper and under surfaces of the intermediate and inner petals.

The general tonality of the newly opened flower is between 53D and 46C with a large zone at the point where the petals attaches of between 8A and 13B.

THREE-DAY-OLD FLOWER

On the under surfaces of the outer, intermediate and inner petals, the color at the base of the petals is between 10D and 9D, gradually suffusing toward the center of the petals with between 155B and 155C often blushed mostly on the outermost petals with between 57C and 63B. At the point where the petal attaches, there is a small zone of near 9C. The upper surface color of the outer, intermediate and inner petals is between 57B and 53C. At the point where the petal attaches, there is a large zone of between 10D and 9D.

The under and upper surface color of the petaloids are similar in coloration to the upper and under surfaces of the intermediate and inner petals.

The general tonality of the three-day-old flower is between 57B and 53C with a large zone at the point where the petals attaches of between 10D and 9D.

On the spent bloom, the petals usually drop off cleanly.

In May in Pomona, Calif., blooms on the bush growing outdoors generally last about four to five days. Cut roses from plants grown outdoors and kept at normal indoor living temperatures generally last about four to five days.

MALE REPRODUCTIVE ORGANS

Stamens are many in number (average about 90) and are arranged regularly about the pistils; a few are mixed with petaloids. The filaments are of medium length (about 0.3 to about 0.6 cm.) most with anthers. Filaments are between 14B and 13A in color. The anthers are moderately small for the class and all open approximately at the same time. Anther color when immature is near 20B on the external part and near 13D on the internal part. Anther color at maturity is near 164C on the external part and near 165A on the internal part. Pollen is moderately abundant and near 18B in color.

FEMALE REPRODUCTIVE ORGANS

Pistils vary in number (average about 35). The styles are even, moderately short in length (about 0.4 to about 0.5 cm.), somewhat thin in caliper, and loosely bunched to somewhat columnar. Stigma color is between 10B and 11B. Style color is between 151B and 145B usually moderately suffused near the top with between 53B and 53C. Ovaries are usually all enclosed in the calyx.

Hips have not been observed on this variety when grown in Pomona, Calif.

FOLIAGE

The compound leaves are usually comprised of three to seven leaflets and are borne abundantly. The five-leaflet leaves are about 5.0 to about 9.1 cm. in length and about 3.8 to about 6.2 cm. in width at the widest point, moderately heavy to crisp in texture, and semi-glossy in finish. The terminal leaflets are about 2.4 to about 3.9 cm. in length and about 1.4 to about 2.3 cm. in width at the widest point, shaped moderately ovate to somewhat oval with acuminate to somewhat acute apices and rounded bases. Their margins are usually simply serrate.

The upper surface color of the mature leaf is between 137A and 147A. The under surface color of the mature leaf is between 147B and 148A. The upper surface color of the young leaf is between 146B and 144A, often moderately suffused especially on the edge with between 187B and 183B. The under surface color of the young leaf is between 138B and 144A, sometimes moderately suffused with between 187B and 183B.

The rachis is somewhat light in caliper and usually mostly smooth but sometimes rough. The upper side is shallowly grooved with some hairs and very few stipitate glands on the edges of the grooves. The under side of the rachis is usually mostly smooth but sometimes rough with some hairs and sometimes small prickles. The rachis color is near 146B on the under side and near 137B on the upper side.

The stipules are about 0.9 to about 1.4 cm. in length and of moderately wide width (about 0.3 to about 0.5 cm.) with medium length straight points that usually turn out at an angle of more than 45 degrees and sometimes recurve toward the stem. The stipule color is between 146B and 137B often moderately suffused with between 187B and 187A.

The petiole is somewhat light in caliper and usually mostly smooth but sometimes rough. The upper side is shallowly grooved with some hairs and very few stipitate glands on the edges of the grooves. The under side of the petiole is usually mostly smooth but sometimes rough with some hairs and sometimes small prickles. The petiole is about 0.4 to about 1.2 cm. in length and about 0.1 to about 0.15 cm in diameter at the widest point. The petiole color is near 146B on the under side and near 137B on the upper side.

The plant displays an above average degree of resistance to powdery mildew and rust as compared to other commercial varieties grown under comparable conditions in Pomona, Calif. The plant's winter hardiness and drought/heat tolerance are yet to be determined.

GROWTH

The plant has a bushy compact moderately upright low growing habit (about 46 to about 56 cm. in height and about 36 to about 46 cm. spread at the widest point), with very full branching. It displays moderately vigorous growth and the canes are of medium to somewhat small caliper for the class.

The color of the major stems is between 148A and 147B. They bear few large prickles that are about 0.5 to about 0.7 cm. in length. The large prickles are angled slightly downward with a moderately long narrow oval base; prickle color is between 165C 164B. The major stem bears very few small prickles of similar shape and coloration.

The color of the branches is between 137B and 147A sometimes moderately suffused, especially on the side exposed to the sun, with between 187A and 187B. They bear few large prickles which are of similar size and shape to the large prickles on the major stems; prickle color is between 151A and 153A sometimes moderately suffused with near 185B. The branches bear very few small prickles of similar shape and coloration.

The color of the new shoots is between 146B and 144A sometimes moderately suffused with between 187A and 187B. They bear very few large prickles which are of similar size and shape to the large prickles on the major stems; prickle color is between 151A and 153A sometimes moderately suffused with near 185B. The shoots bear very few small prickles of similar shape and coloration.

I claim:

1. A new and distinct Miniature rose plant of the variety substantially as described and illustrated herein.

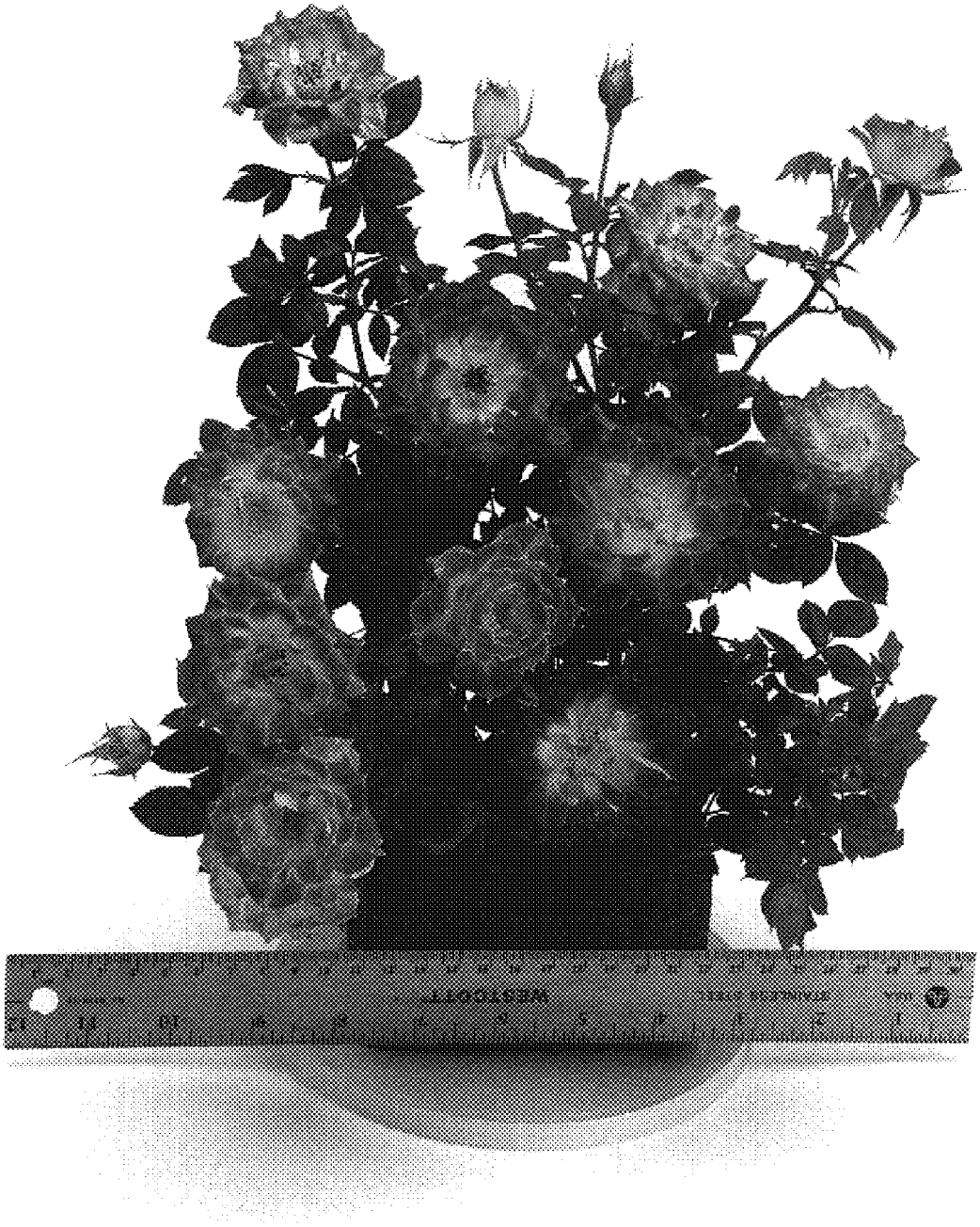

* * * * *